(12) United States Patent  (10) Patent No.: US 8,052,742 B2
White et al.  (45) Date of Patent: *Nov. 8, 2011

(54) INTRALUMINAL GRAFT

(75) Inventors: Geoffrey H. White, East Balmain (AU); Welyun Yu, Five Dock (AU)

(73) Assignee: Gore Enterprise Holding, Inc.DE (US)

( * ) Notice: Subject to any disclaimer, the term of this patent is extended or adjusted under 35 U.S.C. 154(b) by 853 days.

This patent is subject to a terminal disclaimer.

(21) Appl. No.: 11/556,788

(22) Filed: Nov. 6, 2006

(65) Prior Publication Data

US 2007/0067024 A1  Mar. 22, 2007

Related U.S. Application Data

(63) Continuation of application No. 10/733,292, filed on Dec. 12, 2003, now abandoned, which is a continuation of application No. 09/478,352, filed on Jan. 6, 2000, now Pat. No. 6,689,158, which is a continuation of application No. 09/071,731, filed on May 1, 1998, now Pat. No. 6,582,458, which is a continuation of application No. 08/446,672, filed as application No. PCT/AU94/00586 on Sep. 29, 1994, now Pat. No. 5,782,904.

(30) Foreign Application Priority Data

Sep. 30, 1993 (AU) ...................... PM1537

(51) Int. Cl.
*A61F 2/06* (2006.01)
(52) U.S. Cl. ...................... 623/1.36; 623/1.13
(58) Field of Classification Search .................. 623/1.13
See application file for complete search history.

(56) References Cited

U.S. PATENT DOCUMENTS

| 3,304,557 A | 2/1967 | Polansky |
| 3,868,956 A | 3/1975 | Alfidi et al. |
| 3,878,565 A | 4/1975 | Sauvage |
| 3,890,977 A | 6/1975 | Wilson |
| 3,996,938 A | 12/1976 | Clark, III |
| 4,130,904 A | 12/1978 | Whalen |
| 4,149,911 A | 4/1979 | Clabburn |
| 4,225,979 A | 10/1980 | Rey |
| 4,306,318 A | 12/1981 | Mano |
| 4,416,028 A | 11/1983 | Eriksson et al. |
| 4,425,908 A | 1/1984 | Simon |

(Continued)

FOREIGN PATENT DOCUMENTS

AU 649051 1/1992

(Continued)

OTHER PUBLICATIONS

Yoshioka et al. "Self-Expanding Endovascular Graft: An Experimental Study in Dogs" AJR:151, Oct. 1988, pp. 673-676.

(Continued)

*Primary Examiner* — Anhtuan Nguyen
*Assistant Examiner* — Sarah Simpson

(57) ABSTRACT

An intraluminal graft includes a tubular graft body extending along a cylindrical axis, a plurality of wires spaced apart from each other and arranged to circumferentially reinforce said tubular graft body along a substantial portion of its length, and a body surface including an inner surface region and an outer surface region. The body surface defines a plurality of apertures extending from an exterior space, and a first portion of a first wire is in the interior space while a second portion of the first wire is in the exterior space.

25 Claims, 4 Drawing Sheets

U.S. PATENT DOCUMENTS

| | | | |
|---|---|---|---|
| 4,503,569 A | 3/1985 | Dotter |
| 4,512,338 A | 4/1985 | Balko et al. |
| 4,553,545 A | 11/1985 | Maass |
| 4,560,374 A | 12/1985 | Hammerslag |
| 4,562,596 A | 1/1986 | Kornberg |
| 4,577,631 A | 3/1986 | Kreamer |
| 4,580,568 A | 4/1986 | Gianturco |
| 4,617,932 A | 10/1986 | Kornberg |
| 4,649,922 A | 3/1987 | Wiktor |
| 4,655,771 A | 4/1987 | Wallsten |
| 4,665,906 A | 5/1987 | Jervis |
| 4,665,918 A | 5/1987 | Garza |
| 4,681,110 A | 7/1987 | Wiktor |
| 4,728,328 A | 3/1988 | Hughes |
| 4,729,766 A | 3/1988 | Bergentz |
| 4,731,073 A | 3/1988 | Robinson |
| 4,732,152 A | 3/1988 | Wallsten |
| 4,733,665 A | 3/1988 | Palmaz |
| 4,739,762 A | 4/1988 | Palmaz |
| 4,762,128 A | 8/1988 | Rosenbluth |
| 4,768,507 A | 9/1988 | Fischell et al. |
| 4,772,264 A | 9/1988 | Cragg |
| 4,776,337 A | 10/1988 | Palmaz |
| 4,787,899 A | 11/1988 | Lazarus |
| 4,793,348 A | 12/1988 | Palmaz |
| 4,800,882 A | 1/1989 | Gianturco |
| 4,820,298 A | 4/1989 | Leveen |
| 4,830,003 A | 5/1989 | Wolff et al. |
| 4,856,516 A | 8/1989 | Hillstead |
| 4,872,874 A | 10/1989 | Taheri |
| 4,878,906 A | 11/1989 | Lindemann |
| 4,886,062 A | 12/1989 | Wiktor |
| 4,886,065 A | 12/1989 | Collins, Jr. |
| 4,913,141 A | 4/1990 | Hillstead |
| 4,922,905 A | 5/1990 | Strecker |
| 4,923,464 A | 5/1990 | DiPisa, Jr. |
| 4,950,227 A | 8/1990 | Savin et al. |
| 4,954,126 A | 9/1990 | Wallsten |
| 4,969,458 A | 11/1990 | Wiktor |
| 4,969,890 A | 11/1990 | Sugita |
| 4,994,071 A | 2/1991 | MacGregor |
| 5,015,253 A | 5/1991 | MacGregor |
| 5,019,085 A | 5/1991 | Hillstead |
| 5,019,090 A | 5/1991 | Pinchuk |
| 5,035,706 A | 7/1991 | Gianturco |
| 5,037,392 A | 8/1991 | Hillstead |
| 5,037,427 A | 8/1991 | Harada |
| 5,041,126 A | 8/1991 | Gianturco |
| 5,047,050 A | 9/1991 | Arpesani |
| 5,057,092 A | 10/1991 | Webster |
| 5,061,275 A | 10/1991 | Wallsten et al. |
| 5,064,435 A | 11/1991 | Porter |
| 5,067,957 A | 11/1991 | Jervis |
| 5,078,726 A | 1/1992 | Kreamer |
| 5,078,736 A | 1/1992 | Behl |
| 5,085,635 A | 2/1992 | Cragg |
| 5,102,417 A | 4/1992 | Palmaz |
| 5,104,399 A | 4/1992 | Lazarus |
| 5,104,404 A | 4/1992 | Wolff |
| 5,108,416 A | 4/1992 | Ryan et al. |
| 5,116,318 A | 5/1992 | Hillstead |
| 5,122,154 A | 6/1992 | Rhodes |
| 5,123,917 A * | 6/1992 | Lee .......................... 623/22.26 |
| 5,133,732 A | 7/1992 | Wiktor |
| 5,135,536 A | 8/1992 | Hillstead |
| 5,151,105 A | 9/1992 | Kwan-Gett |
| 5,161,547 A | 11/1992 | Tower |
| 5,163,958 A | 11/1992 | Pinchuk |
| 5,178,630 A | 1/1993 | Schmitt |
| 5,183,085 A | 2/1993 | Timmermans |
| 5,192,297 A | 3/1993 | Hull |
| 5,192,307 A | 3/1993 | Wall |
| 5,195,984 A | 3/1993 | Schatz |
| 5,201,901 A | 4/1993 | Harada |
| 5,207,695 A | 5/1993 | Trout, III |
| 5,211,658 A | 5/1993 | Clouse |
| 5,219,355 A | 6/1993 | Parodi et al. |
| 5,236,446 A | 8/1993 | Dumon |
| 5,246,445 A | 9/1993 | Yachia et al. |
| 5,266,073 A | 11/1993 | Wall |
| 5,275,622 A | 1/1994 | Lazaru |
| 5,282,823 A | 2/1994 | Schwartz et al. |
| 5,282,824 A | 2/1994 | Gianturco |
| 5,282,860 A | 2/1994 | Matsuno et al. |
| 5,290,305 A | 3/1994 | Inoue |
| 5,292,331 A | 3/1994 | Boneau |
| 5,304,200 A | 4/1994 | Spaulding |
| 5,314,472 A | 5/1994 | Fontaine |
| 5,316,023 A | 5/1994 | Palmaz et al. |
| 5,330,500 A | 7/1994 | Song |
| 5,330,528 A | 7/1994 | Lazim |
| 5,342,300 A | 8/1994 | Stefanadis et al. |
| 5,342,387 A | 8/1994 | Summers |
| 5,344,425 A | 9/1994 | Sawyer |
| 5,344,426 A | 9/1994 | Lau et al. |
| 5,354,308 A | 10/1994 | Simon et al. |
| 5,354,309 A | 10/1994 | Schnepp-Pesch |
| 5,356,433 A | 10/1994 | Rowland et al. |
| 5,360,443 A * | 11/1994 | Barone et al. ................ 623/1.13 |
| 5,366,504 A | 11/1994 | Andersen |
| 5,370,683 A | 12/1994 | Fontaine |
| 5,375,612 A | 12/1994 | Cottenceau et al. |
| 5,383,892 A | 1/1995 | Cardon et al. |
| 5,383,928 A | 1/1995 | Scott |
| 5,387,235 A | 2/1995 | Chuter |
| 5,389,106 A | 2/1995 | Tower |
| 5,397,345 A | 3/1995 | Lazarus |
| 5,403,341 A | 4/1995 | Solar |
| 5,405,377 A | 4/1995 | Cragg |
| 5,409,019 A | 4/1995 | Wilk |
| 5,413,597 A | 5/1995 | Krajicek |
| 5,415,664 A | 5/1995 | Pinchuk |
| 5,429,144 A | 7/1995 | Wilk |
| 5,443,496 A | 8/1995 | Schwartz et al. |
| 5,443,497 A | 8/1995 | Venbrux |
| 5,443,498 A | 8/1995 | Fontaine |
| 5,456,713 A | 10/1995 | Chuter |
| 5,464,449 A | 11/1995 | Ryan et al. |
| 5,489,295 A | 2/1996 | Piplani et al. |
| 5,507,767 A | 4/1996 | Maeda |
| 5,507,771 A | 4/1996 | Gianturco |
| 5,522,880 A | 6/1996 | Barone et al. |
| 5,562,724 A | 10/1996 | Vorwerk |
| 5,562,726 A | 10/1996 | Chuter |
| 5,562,727 A | 10/1996 | Turk |
| 5,562,728 A | 10/1996 | Lazarus |
| 5,562,742 A | 10/1996 | Kolp et al. |
| 5,571,170 A | 11/1996 | Palmaz |
| 5,575,817 A | 11/1996 | Martin |
| 5,578,071 A * | 11/1996 | Parodi .......................... 623/1.19 |
| 5,609,605 A | 3/1997 | Marshall et al. |
| 5,609,627 A | 3/1997 | Golcoechea et al. |
| 5,639,278 A | 6/1997 | Dereume et al. |
| 5,676,696 A | 10/1997 | Marcade |
| 5,676,697 A | 10/1997 | McDonald |
| 5,683,449 A | 11/1997 | Marcade |
| 5,683,450 A | 11/1997 | Golcoechea et al. |
| 5,683,451 A | 11/1997 | Lenker et al. |
| 5,683,453 A | 11/1997 | Palmaz |
| 5,693,086 A | 12/1997 | Golcoechea et al. |
| 5,709,713 A | 1/1998 | Evans et al. |
| 5,716,365 A | 2/1998 | Golcoechea et al. |
| 5,718,724 A | 2/1998 | Golcoechea et al. |
| 5,752,522 A | 5/1998 | Murphy |
| 5,782,904 A | 7/1998 | White et al. |
| 5,797,949 A | 8/1998 | Parodi |
| 5,824,039 A | 10/1998 | Piplani et al. |
| 5,824,055 A | 10/1998 | Spirigliozzi et al. |
| 5,860,923 A | 1/1999 | Lenker et al. |
| 5,871,536 A | 2/1999 | Lazarus |
| 6,117,167 A | 9/2000 | Goicoechea et al. |
| 6,165,213 A | 12/2000 | Goicoechea et al. |
| 6,582,458 B1 | 6/2003 | White et al. |
| 6,689,158 B1 | 2/2004 | White et al. |

FOREIGN PATENT DOCUMENTS

| | | |
|---|---|---|
| DE | 1766921 | 9/1970 |
| DE | 2805749 | 2/1978 |
| DE | 9319267.3 | 4/1994 |
| DE | 4303181 | 8/1994 |
| EP | 0145166 | 6/1985 |
| EP | 0183372 | 10/1985 |
| EP | 0177300 | 3/1986 |
| EP | 0335341 | 10/1989 |
| EP | 0421729 | 4/1991 |
| EP | 0423916 | 4/1991 |
| EP | 0466518 | 1/1992 |
| EP | 0472731 | 3/1992 |
| EP | 0508473 | 4/1992 |
| EP | 0508473 | 10/1992 |
| EP | 0540290 | 10/1992 |
| EP | 0521573 | 1/1993 |
| EP | 0556850 | 2/1993 |
| EP | 0539237 | 4/1993 |
| EP | 0541443 | 5/1993 |
| EP | 0579523 | 6/1993 |
| EP | 0551179 | 7/1993 |
| EP | 0556850 | 8/1993 |
| EP | 0579523 | 1/1994 |
| EP | 0617930 | 3/1994 |
| EP | 0621016 | 4/1994 |
| EP | 0646365 | 4/1995 |
| EP | 0656198 | 6/1995 |
| EP | 0686379 | 12/1995 |
| EP | 0461791 | 1/1997 |
| EP | 0792627 | 9/1997 |
| FR | 2333487 | 12/1975 |
| FR | 2409747 | 10/1980 |
| FR | 2512678 | 11/1985 |
| FR | 2678508 | 1/1993 |
| GB | 2106190 | 4/1983 |
| GB | 2189150 | 10/1987 |
| JP | 4-253856 | 9/1992 |
| JP | 5-76603 | 3/1993 |
| SU | 1217402 | 5/1984 |
| SU | 1318235 | 7/1984 |
| SU | 1457921 | 3/1986 |
| WO | WO 83/00997 | 3/1983 |
| WO | WO 83/03752 | 11/1983 |
| WO | WO 89/01320 | 2/1989 |
| WO | WO 89/08433 | 9/1989 |
| WO | WO 90/04982 | 5/1990 |
| WO | WO 91/07928 | 6/1991 |
| WO | WO 91/12047 | 8/1991 |
| WO | WO 92/00043 | 1/1992 |
| WO | WO 92/06734 | 4/1992 |
| WO | WO 93/13825 | 7/1993 |
| WO | WO 94/12136 | 6/1994 |
| WO | WO 94/17754 | 8/1994 |
| WO | WO 95/01761 | 1/1995 |
| WO | WO 95/08966 | 4/1995 |
| WO | WO 95/16406 | 6/1995 |
| WO | WO 96/10375 | 4/1996 |
| WO | WO 96/11648 | 4/1996 |
| WO | WO 96/28116 | 9/1996 |

OTHER PUBLICATIONS

Mar. 1989, Micich et al., "Percutaneously Placed Edovascular Grafts for Aortic Aneurysms: Fesibility Study" Radiology 1989; 170:1033-1037.

Dec. 1992, Laborde, et al. "Intraluminal Bypass of Abdominal Aortic Aneurysm: Feasibility Study" Radiology 1992; 184:185-190.

Charnsangavej et al. "Expandable Stents" Interventional Radiology pp. 692-699, 1990.

2008, In the United States District Court for the Northern District of California No. C 03-03817 JSW Order Granting Cook Incorporated's Motion for Summary Judgment of Non-Infringement.

Cronenwett et al., "Arterial Aneurysms," Rutherford Vascular Surgery Fifth Edition, 2000, title page, copyright page, table of contents for sections X1-XV; and pp. 1241-1246.

Baird et al., "Aortoiliofemoral Occlusive Disease," Vascular Surgery Principles and Practice, 1987, title page, copyright page, table of contents Part 1-4; and pp. 344-352.

Fax cover sheet dated Nov. 11, 1992 showing US destination telephone No. 602-240-6160 and abstract by May et al., "Advantages and Limitations of Intraluminal Grafts for Thoracic and Abdominal Aortic Aneurysms," associated with fax cover sheet.

Brochure for Meeting Announcement and Call for Abstracts for International Congress VI Endovascular Interventions, for Jan. 27-31, 1993.

Preliminary Program for International Congress VI Endovascular Interventions, for Jan. 27-31, 1993.

Official Program for the International Congress VI Endovascular Interventions Tomorrow's Technology Today including 3 abstracts, respectively naming Rees, Fogarty, and G. White as authors, Jan. 27-31, 1993.

White et al., Powerpoint Slide Presentation: "Experimental Endoluminal Grafts and Coated Stents," first page stating "With Compliments Astara and Russell," (6 pages).

White et al., PowerPoint Slide Presentation: "Experimental Endoluminal Grafts and Coated Stents," with first page stating "Geoffrey H. White, Weiyun Yu, George E. Kopchok, Martin R. Back, Rodney A. White, Samuel E. Wilson, James May," (13 pages).

MINTEC Sales literature (5 pages) for Cragg EndoPro System 1, Facsimile date Oct. 1993.

Dotter et al., "Transluminal Expandable Nitinol Coil Stent Grafting: Preliminary Report," Technical Developments and Instrumentation, Radiology 147, pp. 259-260, Apr. 1983.

Cragg et al., "Nonsurgical Placement of Arterial Endoprostheses: A New Technique Using Nitinol Wire," Radiology 147: pp. 261-263, Apr. 1983.

Diagramatic representations of the treatment of occlusive arterial disease by balloon angioplasty and stent implantation, dated Mar. 1993.

Richter, G.M., 1 page excerpt from an article, dated Aug. 1993.

Meeting cover page and agenda for 2nd Annual RPAH Symposium on Endovascular Therapies "Endoluminal Aortic Aneurysm Grafting and Stent Applications in Vascular Disease," Sydney Australia, Nov. 27-28, 1992 (4 pages).

Fax cover sheet, preliminary notice, registration information and attendance list for: "3rd Annual Symposium on Endovascular Therapies for Endoluminal Aneurysm Grafting Vascular Stents and Endovascular Interventions," Nov. 26-27, 1993 (28 pages).

Preliminary program for International Congress VII Endovascular Interventions, Feb. 13-17, 1994.

White et al., Abstract, "A New Non-Stented Balloon-Expandable Graft for Straight or Bifurcated Endoluminal Bypass," after Nov. 1993.

White et al., Abstract, "A Comparison of Four Devices for Endoluminal Repair of Abdominal Aortic Aneurysms," Annual Scientific Conference, May 1994.

ISR for PCT/AU 94/00586, Nov. 30, 1994.

Bard Vascular Systems Division, Product Brochure "USCI DeBakey Soft-Woven Dacron Vascular Prosthesis," 1991.

Mirich, et al., "Percutaneoulsy Placed Endovascular Grafts for Aortic Aneurysms: Feasibility Study," Radiology 1989: 170: 1033-1037.

Balko, et al., "Transfemoral Placement of Intraluminal Polyurethane Prosthesis for Abdominal Aortic Aneurysm," present at the Annual Meeting of the Association for Academic Surgery, Nov. 10-13, 1985.

Oct. 1988, Yoshioka et al., Self-Expanding Endovascular Graft: An Experimental Study in Dogs, American Journal of Radiology, 151, pp. 673-676.

Document Bibliography and Abstract page printout for EP 472731 from EPO website epo@cenet.

Document Bibliography and Abstract page printout for US 5383892 from EPO website epo@cenet.

Document Bibliography and Abstract page printout for US 5562724 from EPO website epo@cenet.

Feb. 18, 2000, Declaration of Geoffrey H. White.

Jun. 17, 2000, Declaration of Ian L. Gordon including Exhibit B.

Feb. 28, 2000, Declaration of W. Davis.

Jun. 16, 2000, Declaration of Mark Dehdashtian.

Apr. 24, 2001, Declaration of Geoffrey H. White.
Nov. 22, 2002, Declaration of Geoffrey H. White including Exhibits GHWI and GHWII.
Mar. 8, 2002, Declaration of Edward B. Diethrich.
Nov. 29, 2002, Declaration of Tim McGahan 2002 including CV of Tim McGahan.
1984, McGraw-Hill Dictionary of Scientific and Technical Terms; Third Edition; MgGraw-Hill Book Company, New York; pp. 796 and 1284.
Duering et al., Editors, "Engineering Aspects of Shape Memory Alloys," London: Butterworth-Heinemann Ltd, 1990, pp. 369-393.
Schetky, "Shape Memory Alloys," Scientific American, Nov. 1979, vol. 241, No. 5, pp. 74-82.
Dondelinger et al., Editors, "Interventional Radiology," New York: Thieme Medical Publishers, Inc., 1990, pp. 686-692.
Cragg et al., "Percutaneous Arterial Grafting," Radiology, vol. 150, No. 1, Jan. 1984, pp. 45-49.
Otsuka et al., "Pseudoelasticity," Metals Forum, vol. 4 No. 3, 1981, pp. 142-152.*
Registration Brochure for: "3rd Annual Symposium on Endoluminal Aneurysm Grafting Stent Applications and Endovascular Interventions," Nov. 25-27, 1993 5 pages).*
Oct. 1993, Marin et al., "Transfemoral Stented Graft Treatment of Occlusive Arterial Disease for Limb Salvage: A Preliminary Report," Circulation, vol. 88 No. 4, p. 11.*
Parodi et al., "Transfemoral Intraluminal Graft Implantation for Abdominal Aortic Aneurysms," Journal of the American College of Cardiology, 21 (Suppl. A): p. 425A, 1993.*
May et al., "Transluminal Placement of a Prosthetic Graft-Stent Device for Treatment of Subclavian Artery Aneurysm," Journal of Vascular Surgery, Dec. 1, 1993, vol. 18, No. 6, pp. 1056-1059.*

May et al., "Treatment of complex Abdominal Aortic Aneurysms by a Combination of Endoluminal and Extraluminal Aortofemoral Grafts," Journal of Vascular Surgery, May 1, 1994, vol. 19 No. 5, pp. 924-933.*
Parodi et al., "Transfemoral Endovascular Treatment of Aortoiliac Aneurysms and Arteriovenous Fistulas with Stented Dacron Grafts," Current Critical Problems in Vascular Surgery, 1993, vol. 5, p. 264.*
Apr. 22, 1993, U.S. Appl. No. 08/051,728, McNamara, "Non-Mitigating Vascular Prosthetics and Minimally Invasive Placement System Therefor."*
1990, Dondelinger et al., Editors, "Interventional Radiology," New York: Thieme Medical Publishers, Inc., 1990, pp. 692-699.*
1991, Parodi et al., "Transfemoral Intraluminal Graft Implementation for Abdominal Aortic Aneurysms," Annals of Vascular Surgery. vol. 5, No. 6, pp. 491-499.*
Dec. 28, 2004, EPO Communication of a Notice of Opposition, Application No./Patent No. 94928713.0-2310/0676937.*
Dec. 20, 2004, EPO Notice of Opposition to a European Patent, Application No./Patent No. 94928713.0-2310/0676937.
Jul. 23, 2007, Claim Construction Order, *Edwards Lifesciences LLC, et al.,* v. *Cook Incorporated, and W.L. Gore and Associates,* in the United States District Court for the Northern District of California, No. C 03-03817 JSW.
Apr. 22, 1993, U.S. Appl. No. 08/051,728, McNamara, "Non-Mitigating Vascular Prosthetics and Minimally Invasive Placement System Therefor."
Sep. 22, 2009, Decision by United States Court of Appeals for the Federal Circuit, 2009-1006, *Edwards Lifesciences LLC and Endogad Research PTY Limited* v. *Cook Incorporated and W.L. Gore & Associates, Inc.*

* cited by examiner

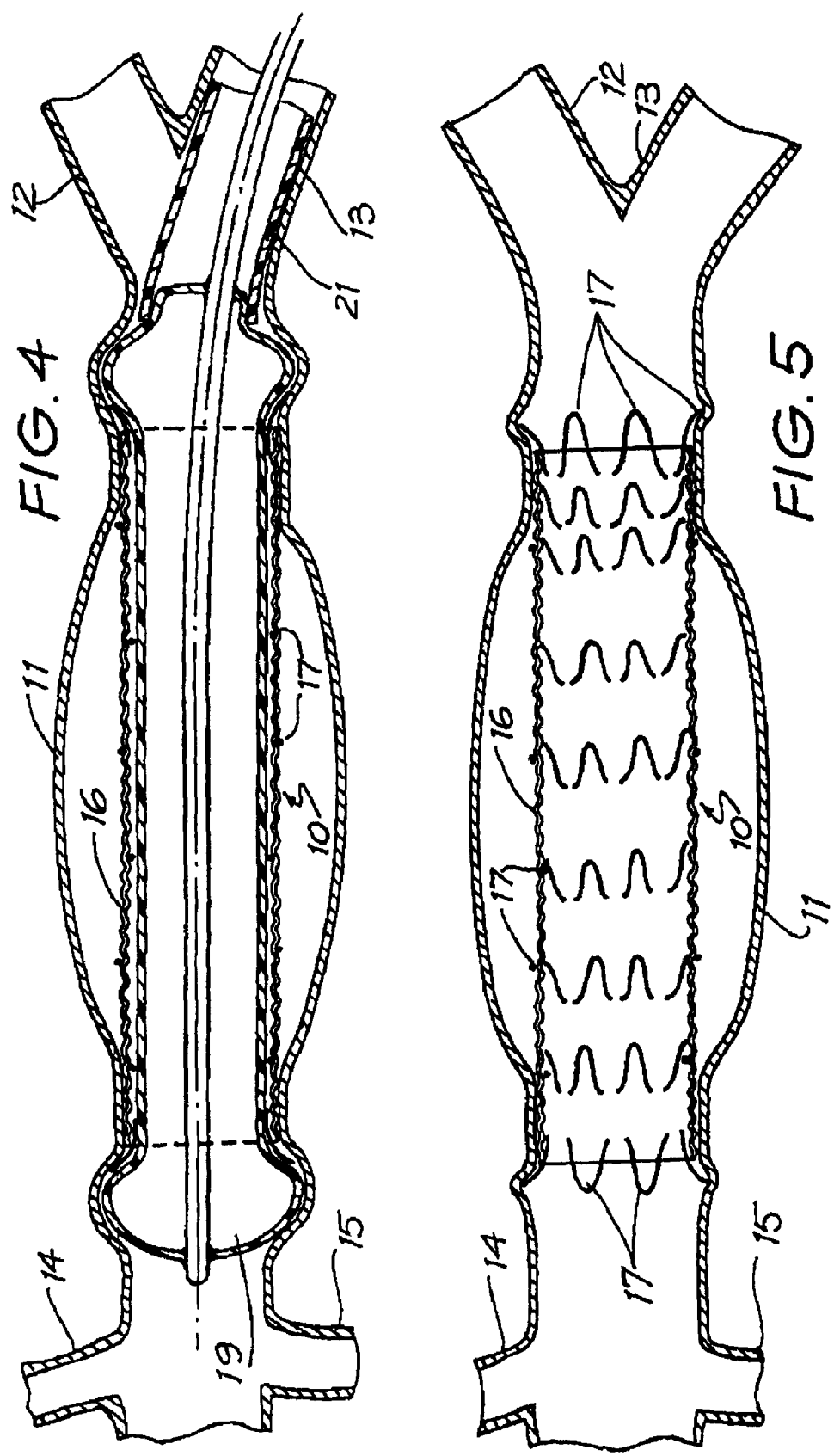

INTRALUMINAL GRAFT

CROSS REFERENCE TO RELATED APPLICATIONS

This application is a continuation of application Ser. No. 10/733,292, filed Dec. 12, 2003, now abandoned which is a continuation of application Ser. No. 09/478,352, filed Jan. 6, 2000, now U.S. Pat. No. 6,689,158, which is a continuation of application Ser. No. 09/071,731, filed May 1, 1998, now U.S. Pat. No. 6,582,458, which is a continuation of application Ser. No. 08/446,672, filed Jul. 20, 1995, now U.S. Pat. No. 5,782,904, which is the National Stage of International Application PCT/AU94/00586, filed Sep. 29, 1994, which claims the benefit of priority of Australian Application No. PM 1537, filed Sep. 30, 1993. The contents of application Ser. No. 10/733,292, filed Dec. 12, 2003 is incorporated herein by reference.

FIELD OF INVENTION

The present invention relates to an intraluminal graft for use in treatment of aneurysms or occlusive diseases.

It is known to use stents and intraluminal grafts of various designs for the treatment of aneurysms such as aortal aneurysms and for the treatment of occlusive diseases such as the occlusion of blood vessels or like ducts such as the bile duct and the ureter (which are all hereinafter called "vessels"). It is known to form such an intraluminal graft of a sleeve in which is disposed a plurality of self expanding wire stents (see Balko A. et al., "Transfemoral Placement of Intraluminal Polyurethane Prosthesis for Abdominal Aortic Aneurysms", Journal of Surgical Research 40, 305-309 (1986); Mirich D. et al, "Percutaneously Placed Endovascular Grafts for Aortic Aneurysms: Feasibility Study" Radiology, Vol. 170, No. 3, part 2, 1033-1037 (1989)). Such intraluminal grafts are inserted through the femoral artery into the aorta in a catheter. Upon the release of the graft from the catheter it expands to the size of the aorta above and below the aneurysms and bridges the aneurysms.

There are a number of problems associated with such known grafts. These include the problem of twisting or kinking of the graft when it has to extend along a non-linear path which, twisting or kinking can lead to occlusion of the lumen of the grafts lack of precise control of the expansion of the graft in the lumen; avoidance of inadvertent separation of a supporting stent and the covering sleeve; and maintaining the graft against longitudinal movement along the lumen in which it is placed. The present invention is directed to an alternative form of intraluminal graft which provides an alternative to the known grafts.

DISCLOSURE OF THE INVENTION

In a first aspect the present invention consists in an intraluminal graft comprising a tubular graft body which is circumferentially reinforced along its length by a plurality of separate, spaced-apart, maleable wires, each of which has a generally cloned sinusoidal or zig-zag shape, one of the wires being located adjacent to one end of the graft body such that alternate crests or apices of the wire projects beyond at least part of that end.

In another aspect the invention relates to a method for positioning an intraluminal graft as defined above comprising introducing a catheter into a vein, artery or other vessel in the body, causing an intraluminal graft as defined above to be carried through the catheter on an inflatable balloon until the graft extends into the vessel from the proximal end of the catheter, inflating the balloon to cause the alternate crests or apices of the one wire to be urged into contact with the wall of the vessel, deflating the balloon and withdrawing the balloon and the catheter from the vessel.

In preferred embodiments of the invention each end of the graft will be provided with a wire which has alternate crests or apices extending beyond the adjacent end of the graft body. While the graft will normally have wires at each end of the graft with their crests extending beyond the graft body it may be necessary or desirable for a surgeon to shorten a graft and this may be achieved by cutting off part of the graft body. In this case the graft will have extending crests at only one end.

The projection of alternate crests or apices of the end wire or wires beyond at least part of the end or ends of the graft body is an important feature of this invention. As the graft is expanded by a balloon the expansion of the wires, and of the balloon, will be limited by the diameter of the tubular graft body except in the region of the alternate crests or apices of the end wire or wires. The balloon will be able to expand these crests slightly more than the remainder of the wire so that they bell outwardly away from the adjacent end of the graft body. The crests are forced into contact with the wall of the vessel and thereby become at least partly embedded into the vessel wall. This belling out of the crests of the wires at one or both ends of the graft body into contact with the inside surface of the vessel wall and then being at least partly embedded in the wall will assist in resisting any tendency for the graft to move longitudinally within the vessel after insertion. The wire crests may extend across the lumen of a vessel opening into the vessel in which the graft is being placed without occluding that lumen. This allows the intraluminal graft to be used in situations in which the aneurysm to be bridged commences closely adjacent divergent blood vessels. In most cases there will be crests of wire actually projecting totally beyond the end of the graft materials. It would, however, be possible to have flaps of graft material protruding up the outside of each crest even though intermediate the crests the end of the graft stops well short of the crests. In this latter arrangement the crests are still free to bell outwardly as has been described above even though the crests do not extend absolutely beyond the end of the graft.

It is preferred that the one wire has a greater amplitude than at least the next adjacent one or two wires. This allows the wires at the end of the graft to be positioned more closely together than would be the case if they were all of the same amplitude. It is desirable to space the wires adjacent the and of the graft that will be placed "upstream" in the patient as close together as is possible as the neck of the aneurysm with which the graft is engaged can be quite short. Close spacing of the wires maximises the number of wires reinforcing that part of the graft in contact with the neck of the aneurysm. The spacing of the rest of the wires is desirably greater than those adjacent the one end of the graft as this avoids unnecessarily reducing the flexibility of the graft.

The wavelength of the wires in the graft is preferably substantially the same when compressed however when expanded the end wires will have a shorter wavelength than the intermediate wires as the intermediate wires will not bear against the arterial wall and may therefore be more fully expanded.

It is preferred that the edge of the one end of the graft is scooped out or scalloped between each projecting crest of the one wire. This reduces the possibility that a piece of the graft between those crests could project into the arterial lumen and partially occlude it or direct blood around the outside of the graft.

The tubular graft body is preferably formed of a thin biocompatible material such an Dacron or PTFE. The tube material is preferably crimped along its length to increase its flexibility, however, uncrimped material may be used in suitable circumstances. In preferred embodiments of the invention the graft body may be formed from a material having a limited amount of diametric elasticity to ensure that it can be expanded into contact with the vessel wall. The length and diameter of the graft body will be determined by the individual circumstances of the application to which the intraluminal graft is to be put. Typically, the vessel will be assessed by X-ray or other similar examination and a suitably dimensioned graft selected for that application.

The wires are preferably formed of stainless steel or another metal or a plastic which is maleable and is biocompatible. Each wire is preferably woven into the fabric of the graft body to integrate the body and the reinforcing wires. This prevents any possibility of the wire reinforcement separating from the graft body during introduction of the graft or throughout its life. If the graft body is of a woven material the wires may be interwoven with the graft body during its production or alternatively they may be interwoven with the graft body after its manufacture. If the graft body is not woven but is knitted or of an impervious sheet material then the wires may be threaded through suitable holes formed in the graft body. The interweaving of the wires with the graft body has been found to be particularly desirable as it prevents separation of the wires from the graft body which could have serious adverse consequences. It has also been found that this technique is very good for causing the graft to expand effectively with the wires.

In alternative embodiments the wires may be held in place by sutures or adhesives or may be sandwiched between layers of a multi-layered tubular graft body. In all of the foregoing arrangements the wires are preferably disposed substantially within the graft body. It is, however, within the ambit of the invention that the wires may be connected to, and be disposed on, the outside surface of the graft body.

The intraluminal grafts according to this invention may be used to treat aneurysms or occlusive disease. In addition to treating aortic aneurysms they are particularly suitable for treating aneurysms of the femoral artery, the popliteal artery, the thoracic segment of the aorta, visceral arteries such as the renal and mesenteric arteries, the iliac artery and the subclavian artery. The presence of the metal wires in the intraluminal grafts according to this invention assists in placing the graft as the wires are X-ray detectable. As the wires are arrayed along the length of the graft the complete position of the graft in the body can be continuously monitored.

The grafts according to this invention are typically substantially of constant diameter along their length is, they are substantially cylindrical. It is possible, however, for the grafts to be frusto-conical in shape with a diameter that increases, or decreases, along the length of the graft.

The ends of the wires are joined together to form a tail which is preferably on the outside of the graft body and is positioned to lie along its radially outer surface. The ends may be joined by welding, by being twisted together or in any other suitable manner. The ends of the wires may inadvertently perforate the vessel in which the graft is placed, however, any such perforation will be occluded by the graft body thus ensuring that such a perforation will not adversely affect the patient. The ends of adjacent wires are preferably spaced apart radially about the graft body so as not to affect its flexibility and to avoid a line of ends engaging the wall of the vessel. The ends of adjacent wires preferably project in opposite directions along the vessel body. When the intraluminal graft is inserted into a vessel those wire ends which engage the inside surface of the vessel wall will assist in preventing the graft from inadvertent movement along the vessel. Causing the end of alternate wires to project in opposite longitudinal directions along the graft body will assist in preventing longitudinal movement of the graft along the vessel in either direction.

In some circumstances it is desirable to insert two or more overlapped intraluminal grafts according to the present invention. In this case the first or upstream graft preferably has at its downstream end a "skirt" without reinforcing wires. This skirt is typically 10 to 15 mm in length. The second or downstream graft is inserted into the downstream end of the first graft and is expanded to engage with it. There is preferably an overlap of at least 10 mm however the degree of overlap is often adjusted so that the downstream end of the second graft is correctly placed in the downstream neck of the aneurysm being treated. This can lead to a greater overlap than is the minimum required but is a useful technique to ensure that the overall length of the graft is correct.

It is sometimes the case that the aneurysm extends up to or slightly beyond an arterial bifurcation. In such a case it is possible to place a graft according to the present invention which has a bifurcation at its downstream end, a so-called "trouser graft", wholly within the primary artery. A supplemental graft may then be introduced through each of the subsidiary arteries and overlapped with the respective lumenae of the bifurcated part of the primary graft. In the case of an aneurysm in the aorta, for instance, that extended into each of the iliac arteries the primary graft of the "trouser" type would be placed in the aorta through one of the iliac arteries. Supplemental grafts which dock with the bifurcated end of the primary graft would then be inserted through each of the iliac arteries.

In those cases where one graft according to this invention is to be inserted into the downstream and of another such graft it may be desirable to provide means to stop the "skirt" on the downstream end of the other graft from being distorted by the insertion of the one graft. This may conveniently be done in one or other of two ways. The skirt may be provided with a small number of linear reinforcement wires extending longitudinally of the graft. In this case, the wires are spaced about the circumference of the skirt. Alternatively, the skirt may be provided with at least one resilient annular reinforcement wire. The resilient reinforcement wire will spring into an expanded condition upon being released from the catheter through which it is introduced into the body. This latter arrangement is particularly suitable in the case of "trouser grafts" wherein one leg of the graft will have a skirt which cannot be expanded by a balloon catheter.

BRIEF DESCRIPTION OF DRAWINGS

Hereinafter given by way of example is a preferred embodiment of the present invention described with reference to the accompanying drawings, in which:

FIG. 4 is a detailed longitudinal sectional view through the intraluminal graft of FIG. 2 as it is being expanded into contact with the aorta of a patient during placement;

FIG. 5 is a detailed longitudinal sectional wire through the intraluminal graft of FIG. 2 after it has been inserted into the aorta of a patient;

BEST MODE OF CARRYING OUT THE INVENTION

Figure 1:
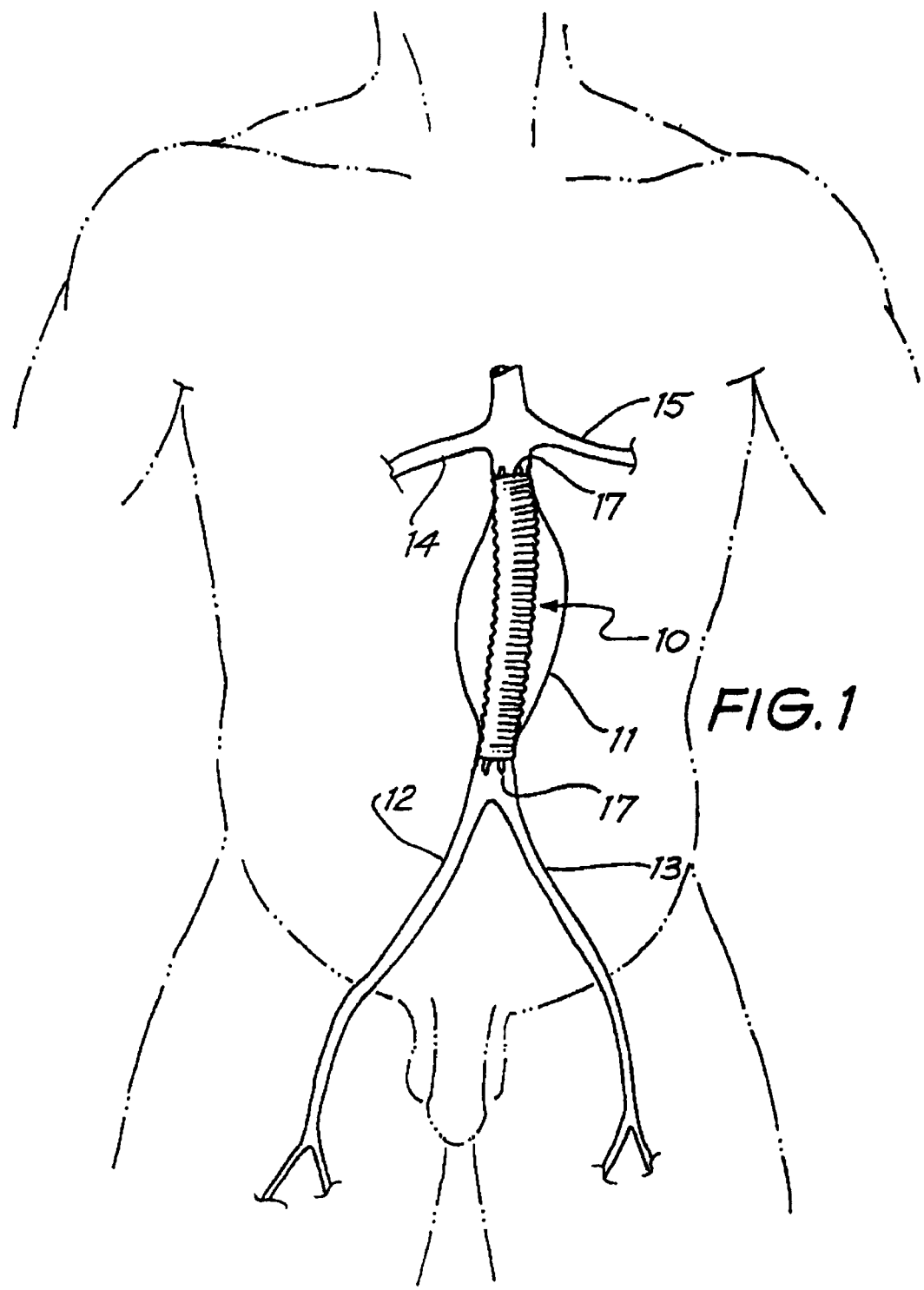
FIG. 1 is a diagrammatic partially cut-away ventral view of a patient with an aortic aneurysm which has been bridged by an intraluminal graft according to the present invention.
Figure 2:
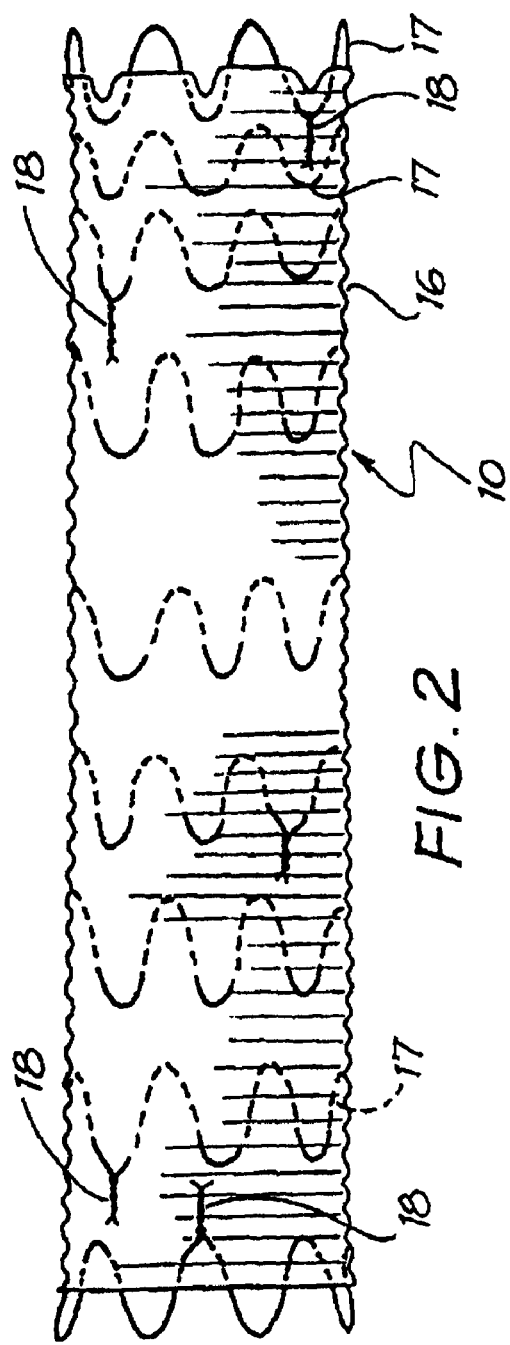
FIG. 2 is a side elevational view of the intraluminal graft of FIG. 1.
Figure 3:
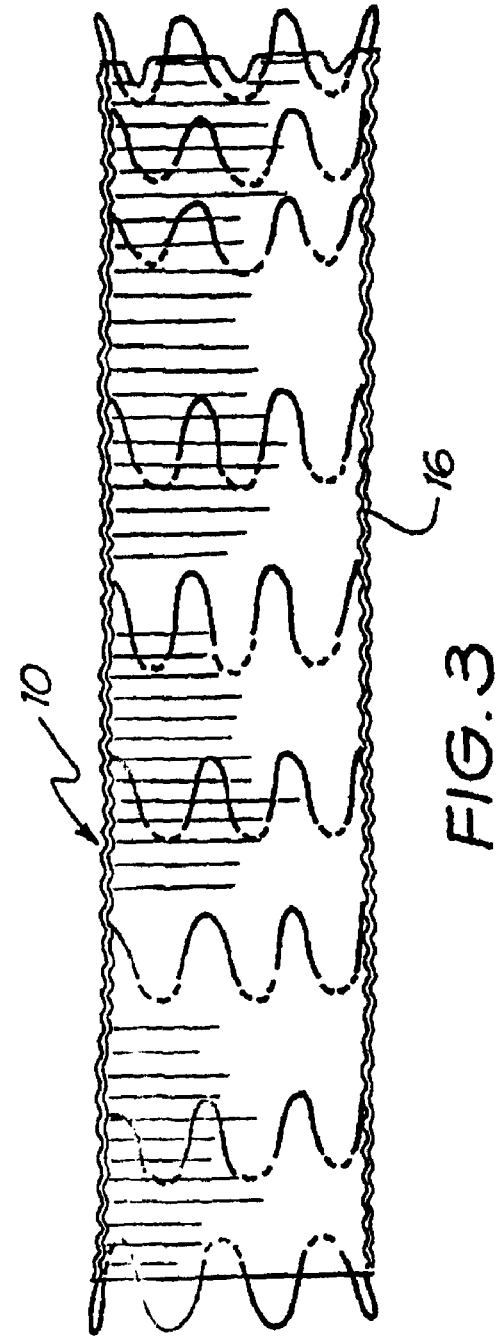
FIG. 3 is a longitudinal sectional view through the intraluminal graft of FIG. 2.
Figure 7:
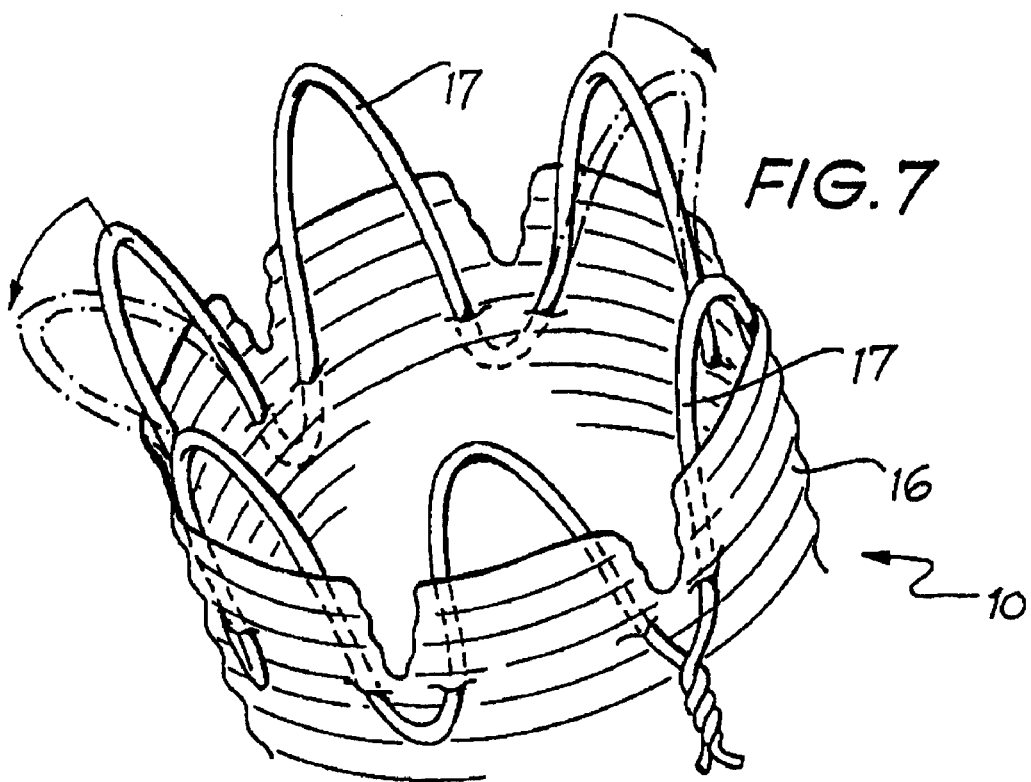
FIG. 7 is a detailed perspective view of the one end of the intraluminal graft of FIG. 6 showing how the alternate crests of the end wire of the graft are pushed radially outwardly during insertion of the graft.
Figure 6:
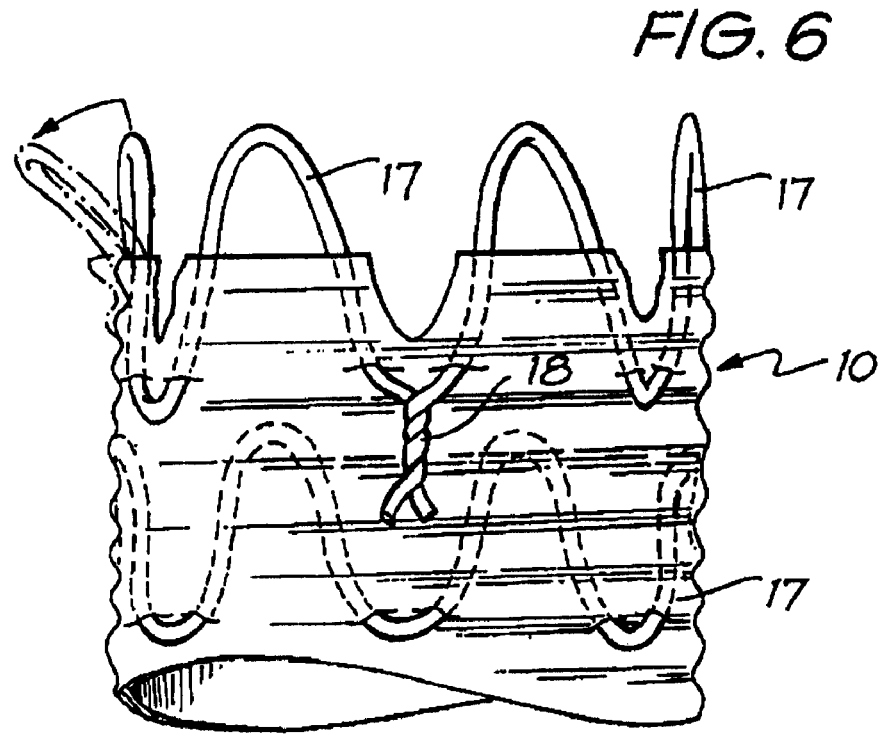
FIG. 6 is a detailed elevational view of one end of the intraluminal graft of FIG. 2.

The intraluminal graft 10 is adapted for insertion transfemorally into a patient to achieve bridging and occlusion of the aneurysm present in the aorta. As is seen in FIG. 1 the aorta 11 is connected to the left and right femoral arteries 12 and 13. The aortic aneurysm is located between the renal arteries 14 and 15 and the junctions of the femoral arteries 12 and 13 with the aorta 11. The graft 10 is, as will be described subsequently in more detail, inserted inside a catheter introduced into one of the femoral arteries 12 or 13 in a leg of the patient. Once the catheter is located appropriately with its proximal end in the aorta 11 the graft 10 is ejected from the catheter and expanded so that each end is in intimate contact around its full periphery with the aorta 11. The graft 10 then bridges the aneurysm and isolates any thrombosis or gelatinuous material associated with the aneurysm outside the graft 10 to reduce the risk of embolisation.

The intraluminal graft 10 comprises a crimped tube 16 of woven Dacron. The tube is reinforced along its length by a number of separate and spaced apart stainless-steel wires 17 (each of which has a generally closed sinusoidal shape). The wires 17 are preferably as thin as possible and are typically 0.3 to 0.4 mm in diameter. The wires 17 are maleable and may be bent into any desired shape, is they are not resilient to any substantial extent so that they have to be physically expanded into contact with the aorta rather than expanding by virtue of their own resilience. The wires 17 are each woven into the fabric of the tube 16 such that alternate crests of each wire 17 are outside the tube 16 with the remainder of that wire 17 inside the tube (except in the case of the endmost wires as will be hereinafter described). The ends of each wire 17 are located outside the tube 16 and are twisted together to form a tail 18. The tails 18 of alternate wires 17 are bent to extend in opposite longitudinal directions along the outside surface of the tube 16.

The endmost ones of the wires 17 overhang the respective ends of the tube 17 so that alternate crests of those wires extend longitudinally beyond the end of the tube 16. The endmost wire 17 preferably has an amplitude of about 6 mm and a wavelength such that between six and eight crests are spaced around the circumference of a 22 mm diameter graft. The next two adjacent wires 18 preferably are spaced as close as possible to the wire 17 and respectively have amplitudes of 4 mm and 5 mm. These wires will typically have the same wavelength initially an the wire 17. Thereafter throughout the graft 10 the wires 18 are spaced at 15 mm intervals, have an amplitude of 6 mm, and have substantially the same initial wavelength as the wire 17.

In use the graft 10 is radially compressed about an inflation balloon 19 (see FIG. 4) and the assembly is inserted into the end of a sheath catheter 21. The sheath catheter 21 is inserted in a known manner through the femoral artery into the aorta 11 until the proximal end of the catheter 21 is beyond the proximal and of the aneurysm. The balloon 19 and the collapsed graft 10 disposed on it, are held stationary and the catheter withdrawn until the graft 10 is fully exposed and spans the aneurysm. The balloon is then inflated to expand the graft 10. The diameter of the tube 16 determines the maximum expansions of the majority of the graft 10 and this diameter has been selected in advance by X-ray examination, or the like, to be substantially equal or only very slightly larger than, the diameter of the undistended aorta 11. The balloon is, however, able to expand the alternating crests of the end wires 17 so that they are pushed firmly into contact with the wall of the aorta. These radially outwardly displaced crests serve to more effectively restrain the graft 10 against longitudinal movement relative to the aorta.

The invention claimed is:

1. A method of placing an intraluminal graft in an aortic artery, comprising:
    positioning, in said aortic artery, an intraluminal graft;
    wherein said intraluminal graft includes a wire apice connected to a first graft body;
    wherein said wire apice extends from an aortic artery first region of said aortic artery, said aortic artery first region being between a femoral artery and a renal artery, to an aortic artery second region, said aortic artery second region being on an opposite side of said renal artery from said femoral artery, wherein said renal artery has an opening where said renal artery joins said aortic artery, and such that said wire apice extends across said opening of said renal artery.

2. The method of claim 1 wherein said first graft body does not occlude said renal artery.

3. The method of claim 1 wherein said first graft body resides in said aortic artery below said renal artery.

4. The method of claim 3 wherein said first graft body resides between said renal artery and said femoral artery.

5. The method of claim 1 wherein said positioning places graft body material of said intraluminal graft facing an aneurysm.

6. The method of claim 1 wherein said positioning places graft body material of said intraluminal graft facing an occlusion.

7. The method of claim 1 wherein said first graft body has a tubular shape.

8. The method of claim 1 wherein said positioning comprises pressing said wire apice against an inner surface of said aortic artery using a balloon.

9. The method of claim 1 wherein said wire apice is part of a first wire, and said first wire has a shape that is generally closed sinusoidal.

10. The method of claim 1 wherein said wire apice is part of a first wire, and said first wire has a shape that is generally closed zig-zag.

11. The method of claim 1 wherein said wire apice is part of a first wire, and further comprising at least a second wire not at an end of said intraluminal graft.

12. The method of claim 11 wherein said first wire forms a closed loop and said second wire forms a closed loop.

13. The method of claim 12 wherein said first wire and said second wire are not connected by wire to one another.

14. The method of claim 1 wherein said wire apice is part of a first wire, and further comprising at least a second wire not at an end of said first graft body and a third wire not at an end of said first graft body.

15. The method of claim 14 wherein said first wire, said second wire, and said third wire are not connected by wire to one another.

16. The method of claim 1 wherein said wire apice is part of a first wire, and wherein said wire apice is one of a plurality of wire apices of said first wire, and wherein at least two of said plurality of wire apices extend beyond said first graft body.

17. The method of claim 1 further comprising securing said intraluminal graft in place in said aortic artery while said wire apice extends from said aortic artery first region to said aortic artery second region, wherein said securing comprises forcing said wire apice into contact with an inside surface of said aortic artery.

18. A method of placing a prosthesis in an aortic artery, said prosthesis having a first end and a second end, said prosthesis comprising a graft body and a wire structure, said wire structure including a plurality of wire apices that extend beyond said first end, said method comprising:
    positioning said prosthesis such that said plurality of wire apices extend across an opening of a renal artery, such that said graft body does not occlude said renal artery, wherein said opening is where said renal artery joins said aortic artery.

19. The method of claim 18 further comprising expanding a balloon to press said wire apices against an inner surface of said aortic artery.

20. A method of placing a prosthesis in an aortic artery, said prosthesis having a first end and a second end, said prosthesis comprising a graft body and a wire structure, said wire structure including a plurality of wire apices that extend beyond said first end, said method comprising:
    positioning said prosthesis such that said plurality of wire apices extend across an opening of a renal artery, such that said graft body does not reside in said renal artery, wherein said opening is where said renal artery joins said aortic artery.

21. The method of claim 20 further comprising expanding a balloon to press said plurality of wire apices against an inner surface of said aortic artery.

22. A method of placing a prosthesis in an aortic artery, said prosthesis having a first end and a second end, said prosthesis comprising a graft body and a wire structure, said wire structure including a plurality of wire apices that extend beyond said first end, said method comprising:
    positioning said prosthesis such that said plurality of wire apices extend across an opening of a renal artery, such that said graft body does not face said renal artery, wherein said opening is where said renal artery joins said aortic artery.

23. The method of claim 22 further comprising expanding a balloon to press said plurality of wire apices against an inner surface of said aortic artery.

24. A method of placing a prosthesis in an aortic artery, said prosthesis having a first end and a second end, said prosthesis comprising a graft body and a wire structure, said wire structure including a plurality of wire apices that extend beyond said first end, said method comprising:
    positioning said prosthesis such that said plurality of wire apices extend across an opening of a renal artery, such that said graft body is not in an intersection of said aortic artery with said renal artery, wherein said opening is where said renal artery joins said aortic artery.

25. The method of claim 24 further comprising expanding a balloon to press said plurality of wire apices against an inner surface of said aortic artery.

* * * * *